(12) United States Patent
Rüdenauer et al.

(10) Patent No.: US 9,920,007 B2
(45) Date of Patent: Mar. 20, 2018

(54) PROCESS FOR THE PREPARATION OF 1-(2,6,6-TRIMETHYLCYCLOHEXYL)-ALKAN-3-OLS

(71) Applicant: BASF SE, Ludwigshafen (DE)

(72) Inventors: Stefan Rüdenauer, Weinheim (DE); Ralf Pelzer, Fürstenberg (DE); Miriam Bru Roig, Heidelberg (DE); Vijay Narayanan Swaminathan, Chennai (IN); Shrirang Hindalekar, Mumbai Borivali (IN); Nitin Gupte, Thane (IN); Prachin Kolambkar, Mumbai Mumbai (IN)

(73) Assignee: BASF SE (DE), `

( * ) Notice: Subject to any disclaimer, the term of this patent is extended or adjusted under 35 U.S.C. 154(b) by 0 days.

(21) Appl. No.: 15/526,962

(22) PCT Filed: Nov. 17, 2015

(86) PCT No.: PCT/EP2015/076792
§ 371 (c)(1),
(2) Date: May 15, 2017

(87) PCT Pub. No.: WO2016/079103
PCT Pub. Date: May 26, 2016

(65) Prior Publication Data
US 2017/0355670 A1   Dec. 14, 2017

(30) Foreign Application Priority Data
Nov. 18, 2014 (IN) .......................... 5796/CHE/2014

(51) Int. Cl.
| C07C 403/16 | (2006.01) |
| C07C 29/00 | (2006.01) |
| C11B 9/00 | (2006.01) |
| C07C 29/17 | (2006.01) |
| A23L 27/20 | (2016.01) |

(52) U.S. Cl.
CPC .......... C07C 403/16 (2013.01); A23L 27/203 (2016.08); C07C 29/175 (2013.01); C11B 9/0034 (2013.01); C07C 2601/14 (2017.05); C07C 2601/16 (2017.05)

(58) Field of Classification Search
CPC .... C07C 403/16; C07C 29/175; C11B 9/0034
USPC .............................................. 568/822
See application file for complete search history.

(56) References Cited

U.S. PATENT DOCUMENTS

| 4,623,750 | A | 11/1986 | Schulte-Elte et al. |
| 7,019,181 | B2 | 3/2006 | Schatkowski et al. |
| 2002/0082457 | A1 | 6/2002 | Kuhn et al. |
| 2007/0032685 | A1 | 2/2007 | Schatkowski |
| 2015/0313817 | A1 | 11/2015 | Gupte et al. |
| 2016/0213582 | A1 | 7/2016 | Rüdenauer et al. |
| 2016/0332944 | A1 | 11/2016 | Rüdenauer et al. |
| 2017/0037020 | A1 | 2/2017 | Rüdenauer et al. |
| 2017/0037021 | A1 | 2/2017 | Stork et al. |
| 2017/0037022 | A1 | 2/2017 | Stork et al. |
| 2017/0066705 | A1 | 3/2017 | Hickmann et al. |
| 2017/0107166 | A1 | 4/2017 | Limbach et al. |

FOREIGN PATENT DOCUMENTS

| DE | 2455761 A1 | 6/1976 |
| DE | 10062771 A1 | 7/2002 |
| EP | 0118809 A2 | 9/1984 |
| EP | 1400503 A1 | 3/2004 |
| EP | 1749810 A1 | 2/2007 |
| GB | 2028321 A | 3/1980 |
| JP | H11035969 A | 2/1999 |
| JP | H11071312 A | 3/1999 |

OTHER PUBLICATIONS

U.S. Appl. No. 15/308,755, Pelzer et al.
U.S. Appl. No. 15/311,012, Linder et al.
U.S. Appl. No. 15/509,228, Riedel et al.
U.S. Appl. No. 15/509,238, Dimitrova et al.
U.S. Appl. No. 15/514,101, Klos et al.
U.S. Appl. No. 15/514,902, Dehn et al.
U.S. Appl. No. 15/518,791, Thrun et al.
Bauer, K., et al., *Common Fragrances and Flavor Materials,: Preparation, Properties and Uses*, 4th ed., Wiley-VCH: Weinheim, 2001, p. 85.
Hibbert, H., et al., "Condensation of Citral with Ketones and Synthesis of Some New Ionones", Journal of the American Chemical Society, vol. 42, No. 1, (1924), pp. 119-130.
International Search Report for PCT/EP2015/076792 dated Feb. 2, 2016.
Kepler, J., et al., "1,2,4-Trioxanes as Potential Antimalarial Agents", Journal of Medicinal Chemistry, vol. 31, No. 4, (1988), pp. 713-716.
Naves, Y.R., et al., "Etudes sur les matiéres végétales volatiles XXVI. Contribution ála connaissance des ionones", Helvetica Chimica Acta, vol. 26, No. 7, (1943), pp. 2151-2165.
Valla, A., et al., New aromatic annulation reaction via a $C_{14}$ enaminone synthon: synthesis of 'terpenoid-like chalcones', Tetrahedron Letters, vol. 46, No. 39, (2005), pp. 6671-6674.
Written Opinion of the International Searching Authority for PCT/EP2015/076792 dated Feb. 2, 2016.

*Primary Examiner* — Sikarl Witherspoon
(74) *Attorney, Agent, or Firm* — Drinker Biddle & Reath LLP

(57) ABSTRACT

The present invention relates to a process for the preparation of 1-(2,6,6-trimethylcyclohexylyalkan-3-ols, in particular 1-(2,6,6-trimethylcyclohexyl)-hexan-3-ol. The invention further relates to 5-alkoxy-1-(2,6,6-trimethylcyclohexenyl)-1-alken-3-ones and the use of these as a fragrance or as flavor, to a fragrance containing composition and/or a fragranced product containing 5-alkoxy-1-(2,6,6-trimethylcyclohexenyl)-1-alken-3-ones and to a method for imparting or modifying a scent or a flavor to a composition by including said alkoxyalkenones into such composition.

15 Claims, No Drawings

PROCESS FOR THE PREPARATION OF 1-(2,6,6-TRIMETHYLCYCLOHEXYL)-ALKAN-3-OLS

CROSS-REFERENCE TO RELATED APPLICATIONS

This application is a national stage application (under 35 U.S.C. § 371) of PCT/EP2015/076792, filed Nov. 17, 2015, which claims benefit of Indian Application No. 5796/CHE/2014, filed Nov. 18, 2014, both applications of which are incorporated herein by reference in their entirety.

The present invention relates to a process for the preparation of 1-(2,6,6-trimethylcyclohexyl)-alkan-3-ols, in particular 1-(2,6,6-trimethylcyclohexyl)-hexan-3-ol. The invention further relates to 5-alkoxy-1-(2,6,6-trimethylcyclohexenyl)-1-alken-3-ones and the use of these as a fragrance or as flavor, to a fragrance containing composition and/or a fragranced product containing 5-alkoxy-1-(2,6,6-trimethylcyclohexenyl)-1-alken-3-ones and to a method for imparting or modifying a scent or a flavor to a composition by including said alkoxyalkenones into such composition.

BACKGROUND OF THE INVENTION

Fragrances are of great interest especially in the field of cosmetics and also laundry and cleaning detergents. Fragrances of natural origin are mostly expensive, often limited in their available amount and, on account of fluctuations in environmental conditions, are also subject to variations in their content, purity etc. It is therefore of great interest to be able to replace, at least partially, fragrances of natural origin with synthetically obtainable substances.

Synthetic 1-(2,6,6-trimethylcyclohexyl)-alkan-3-ols, such as 1-(2,6,6-trimethyl-cyclohexyl)-pentan-3-ol and 1-(2,6,6-trimethylcyclohexyl)-hexan-3-ol, are valuable aroma chemicals. In particular 1-(2,6,6-trimethylcyclohexyl)-hexan-3-ol has found widespread use in products and compositions, which typically comprise at least one aroma compound, such as in laundry and fabric detergents, soaps, perfumes and the like.

Several methods for the preparation of 1-(2,6,6-trimethylcyclohexyl)-alkan-3-ols are known in the state of the art.

Generally, 1-(2,6,6-trimethylcyclohexyl)-alkan-3-ols are obtained via an aldol condensation of citral (3,7-dimethyl-octa-2,6-dienal) with the corresponding 2-alkanones in the presence of a base, followed by the acid catalyzed cyclization of the corresponding aldol condensation products. The obtained 1-(2,6,6-trimethylcyclohexenyl)-1-alken-3-ones are then hydrogenated to the desired 1-(2,6,6-trimethylcyclohexyl)-alkan-3-ols in known manner.

DE2455761 and EP1400503 for example describe a process for the preparation of 1-(2,6,6-trimethylcyclohexyl)-alkan-3-ols containing a high proportion of trans isomers by hydrogenating the corresponding 1-(2,6,6-trimethylcyclohexenyl)-1-alken-3-ones using Raney nickel.

EP10062771 describes a process for the preparation of 1-(2,6,6-trimethylcyclohexyl)-alkan-3-ols with a high content of trans isomers by hydrogenation of the corresponding 1-(2,6,6-trimethylcyclohexenyl)-1-alken-3-ones using ruthenium catalysts.

1-(2,6,6-Trimethylcyclohexyl)-hexan-3-ol for example is typically obtained following known procedures, e.g. described by Hibbert et al., J. Am. Chem. Soc., 1924, Vol. 46, pp. 119-130, and by Naves et al., Helv. Chim. Acta, 1943, Vol. 26, pp. 2151-2165, which comprises an aldol condensation of citral (3,7-dimethylocta-2,6-dienal) with 2-pentanone in the presence of a base, followed by an acid catalyzed cyclization and the subsequent hydrogenation of the obtained 1-(2,6,6-trimethylcyclohexenyl)-1-hexen-3-one. In an alternative approach, citral is first cyclized to cyclocitral (2,6,6-Trimethyl-1-cyclohexene-1-carboxaldehyde), then condensed with 2-pentanone and subsequently hydrogenated. A detailed overview of the technical synthesis of 1-(2,6,6-trimethylcyclohexyl)-hexan-3-ol starting from citral can be found in H. Surburg and J. Panten, Common Flavor and Fragrance Materials, 4th edition, page 85 and the references cited therein.

EP1749810 A1 describes the preparation of 1-(2,2,6-trimethyl cyclohexyl)-hexan-3-ol with at least 30 wt. % of the corresponding trans-isomers by catalytically hydrogenating 1-(2,6,6-trimethylcyclohexenyl)-1-hexen-3-one in the presence of a rhodium-catalyst.

U.S. Pat. No. 4,623,750 and EP0118809 A2 describe a process for the production of 1-(2,6,6-trimethylcyclohexyl)-hexan-3-ol, where cyclocitral is first hydrogenated to dihydro-cyclocitral and then condensed with 2-pentanone and finally again hydrogenated.

All these methods are based on readily available citral as bulk material, but need to employ expensive 2-alkanones, such as 2-pentanone, or other costly speciality chemicals.

Surprisingly, no method is described for the production of 1-(2,6,6-trimethylcyclohexyl)-hexan-3-ol, which directly starts from the bulk chemicals ionones and acetaldehyde. In general, the use of ionones for aldol reactions with aldehydes is rarely described, and if so, then very strong bases, as e.g. butyllithium (BuLi), are used.

Valla et al., Tetrahedron Letters, 2005, Vol. 46, (39), pp. 6671-6674, describe the reaction of beta-ionone with N,N-dimethylformamide dimethylacetal (DMFDMA) by refluxing the two reagents for several hours. The resulting enaminone is further transferred to 1-(2,6,6-trimethylcyclohexen-1-yl)alkan-1,4-dien-3-ones using alkyllithium or alkylmagnesiumhalides.

Kepler et al., J. Med. Chem., 1988, Vol. 31, pp. 713-716, describe the reaction of beta-ionone with acetaldehyde using very strong bases, i.e. buthyllithium and diisopropylamine. The reaction is performed at −78° C. using THF as the solvent. Apart from the fact that the condensation reaction is performed in an organic solvent in the presence of very strong bases, which are critical for use in large scale production, Kepler et al. do not describe the further conversion of the corresponding condensation product to 1-(2,6,6-trimethylcyclohexen-1-yl)-hexa-1,4-dien-3-one and/or 1-(2,6,6-trimethylcyclo-hexyl)-hexan-3-ol.

SUMMARY OF THE INVENTION

It is an object of the present invention to provide a process for the preparation of 1-(2,6,6-trimethylcyclohexyl)-alkan-3-ols, in particular 1-(2,6,6-trimethylcyclohexyl)-hexan-3-ol, which starts from cheap and readily available starting materials, which is simple (small number of synthetic steps) and which does not require the use of hazardous and/or expensive reagents. The process should provide 1-(2,6,6-trimethylcyclohexyl)-alkan-3-ols, in particular 1-(2,6,6-trimethylcyclohexyl)-hexan-3-ol, in good overall yields.

Surprisingly, said object is achieved by a process for preparing a compound of the general formula (I),

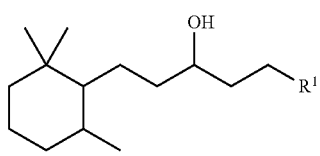

where R¹ is selected from C₁-C₄-alkyl, which comprises
i) reacting a composition containing α-ionone, β-ionone or γ-ionone or mixtures thereof with an aldehyde R¹—(C=O)H in the presence of a base and an alcohol R²—OH to yield a reaction product comprising at least one compound of the general formula (I.a),

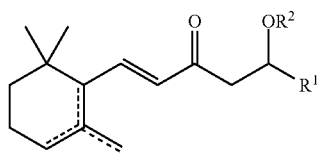

where
R¹ is as defined above and
R² is hydrogen or C₁-C₆-alkyl, and
the broken lines represent a single double bond that can be arranged in one of the three positions drawn,
ii) treating the reaction product obtained in step i) with an acid to yield a ketone of the general formula (I.b)

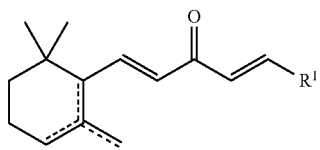

iii) hydrogenating the ketone I.b obtained in step ii) with hydrogen in the presence of a hydrogenation catalyst.

Furthermore, it has surprisingly been found, that the unknown intermediates (1.a), where R¹ is C₁-C₄-alkyl and R² is C₁-C₆-alkyl, exhibit pleasant organo-leptical properties and can advantageously be used as a fragrance or as flavor.

Therefore, the present invention further relates to compounds of the general formula (I.a), where R¹ is C₁-C₄-alkyl and R² is C₁-C₆-alkyl, and to the use of these as a fragrance or as flavor.

The present invention further relates to a fragrance or a flavor composition comprising
a) at least one compound (I.a), where R¹ is C₁-C₄-alkyl and R² is C₁-C₆-alkyl,
b) optionally at least one aroma chemical different from the compounds (I.a), where R¹ is C₁-C₄-alkyl and R² is C₁-C₆-alkyl, and
c) optionally at least one carrier,
with the proviso that the composition comprises at least one of the components b) or c).

The present invention further relates to a product comprising at least one compound (I.a), where R¹ is C₁-C₄-alkyl and R² is C₁-C₆-alkyl, and/or a fragrance or a flavor composition, as defined above, selected from selected from laundry detergents, fabric detergents, cosmetic preparations, fragranced hygiene articles, foods, food supplements, fragrance dispensers, perfumes, pharmaceutical preparations and crop protection compositions.

The invention further relates to a method of imparting or modifying a scent or a flavor to a composition, which method comprises including or incorporating at least one compound of the general formula (I.a), where R¹ is C₁-C₄-alkyl and R² is C₁-C₆-alkyl, into a composition in such an amount that imparts or modifies the scent or flavor of the composition.

The present invention exhibits one or more of the following advantages:
The process of the present invention provides the 1-(2,6,6-trimethylcyclohexyl)-alkan-3-ols, in particular 1-(2,6,6-trimethylcyclohexyl)-hexan-3-ol, in good overall yields.
The present process is simple and efficient providing the 1-(2,6,6-trimethylcyclohexyl)-alkan-3-ols, in particular 1-(2,6,6-trimethylcyclohexyl)-hexan-3-ol, in only three steps from the cheap and readily available ionones.
The present process is characterized by a good atom economy, leaving only water and/or the alcohol R²—OH as the main side products.
The present process does not require the use of hazardous and/or expensive reagents, but surprisingly operates with cheap and simple bases, such as NaOH in alcohols, which can easily be handled safely, even on technical scale.
Due to the abovementioned advantageous features of the present process, 1-(2,6,6-trimethylcyclohexyl)-alkan-3-ols, in particular 1-(2,6,6-trimethylcyclohexyl)-hexan-3-ol, can be provided without difficulty on a large industrial scale.
The compounds of the general formula (I.a), where R¹ is C₁-C₄-alkyl and R² is C₁-C₆-alkyl, possess advantageous sensory properties, in particular a pleasant odor. Therefore, it can be favorably used as a fragrance or as a flavor or as ingredient of a fragrance containing composition and/or a fragrance material.
By virtue of its physical properties, the compounds of the general formula (I.a), where R¹ is C₁-C₄-alkyl and R² is C₁-C₆-alkyl, has particularly good, virtually universal solvent properties for other fragrances and other customary ingredients in fragrance-comprising preparations such as, in particular, perfumes.

DETAILED DESCRIPTION

For the purposes of the present invention, the expression "C₁-C₆-alkyl" comprises straight-chain having from 1 to 6 carbon atoms or branched alkyl groups having from 3 to 6 carbon atoms. Among these are methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl and the like. Preferred C₁-C₆-alkyl comprises straight-chain C₁-C₄-alkyl groups or branched C₃-C₄-alkyl groups.

The expression "C₁-C₆-alkyl" comprises within its definition the expression "C₁-C₄-alkyl".

The 1-(2,6,6-trimethylcyclohexyl)-alkan-3-ols that are obtained by the process of the present invention are compounds of the general formula (I), as defined above.

It is apparent from formula (I) that the carbon atoms of the 1- and 2-position of the cyclohexane-ring as well as the carbon atom at the 3-position of the alkyl chain, which carries the hydroxyl group, may have (R)- or (S)-configuration. Hence, the 1-(2,6,6-trimethylcyclohexyl)-alkan-3-ols can be present in eight different stereoisomers.

Accordingly, the term "1-(2,6,6-trimethylcyclohexyl)-alkan-3-ols" encompasses mixtures comprising all eight stereoisomers of the respective 1-(2,6,6-trimethylcyclohexyl)-alkan-3-ols, where the stereoisomers may be present in equal amounts or wherein at least one of these stereoisomers is present in excess.

Frequently, the 1-(2,6,6-trimethylcyclohexyl)-alkan-3-ols obtained by the present process are mixtures of eight stereoisomers, wherein at least one of these stereoisomers is present in excess.

Generally, the radical $R^1$ in the compounds of the general formulae (I), (I.a) and (I.b) is selected from methyl, ethyl, propyl, isopropyl, n-butyl, isobutyl, sec-butyl, tert-butyl.

Preferably, the radical $R^1$ in the compounds of the general formulae (I), (I.a) and (I.b) is selected from methyl, ethyl n-propyl and isopropyl. Particularly preferred, the radical $R^1$ in the compounds of the general formulae (I), (I.a) and (I.b) is methyl or ethyl.

For the purpose of the present invention, the broken lines drawn in formulae (1.a) and (1.b) represent a single double bond that can be arranged in one of the three positions drawn. Using the nomenclature customary for ionones, this is thus a double bond in an α-, β- or γ-position (see Römpp-Lexikon Naturstoffe, Thieme 1997, page 334-335).

For the purpose of the present invention, the expression "ionone" refers to α-ionone, β-ionone or γ-ionone or to mixtures thereof.

In a preferred embodiment of the present invention, the radical $R^1$ is methyl. Thus, a particularly preferred compound of the general formulae (I) is 1-(2,6,6-trimethylcyclohexyl)-hexan-3-ol.

Step i)

It has surprisingly been found that a simple condensation reaction of a composition containing α-ionone, β-ionone or γ-ionone or mixtures thereof with an aldehyde $R^1$—(C═O)H in the presence of a cheap and simple base and an alcohol $R^2$—OH gives the corresponding beta-hydroxyketones and beta-alkoxyketones of the general formula (I.a) in good yields.

Generally, the condensation reaction is performed in the presence of a strong base. Suitable bases that can be used in the condensation reaction of the present process are mineral bases and/or strong organic bases. Suitable bases are by way of example inorganic bases or base-formers, for example metallic potassium or sodium; hydroxides, hydrides, oxides and amides, of the alkali metals and of the alkaline earth metals. Among these are LiOH, NaOH, KOH, RbOH, CsOH, Mg(OH)$_2$, Ca(OH)$_2$, LiH, NaH, Na$_2$O, sodium amide (NaNH$_2$) or lithium diisopropylamide (LDA).

In a preferred embodiment, step i) of the present process is performed in the presence of metal hydroxides. Preferred metal hydroxides are alkali metal hydroxides or alkaline earth metal hydroxides, for example LiOH, NaOH, KOH, Mg(OH)$_2$ or Ca(OH)$_2$. Particularly preferred metal hydroxides are NaOH and KOH.

Generally, the base used in step i) of the present process is applied in an amount of from 0.5 to 4 equivalents, based on the total molar amount of the ionones present in the reaction mixture. Preferably, the base is applies in an amount of from 0.7 to 2 equivalents, in particular in an amount of from 1 to 1.2 equivalents, based on the total molar amount of the ionones present in the reaction mixture.

The ionone-composition used as starting material for the condensation reaction may comprise pure α-ionone, β-ionone or γ-ionone or mixtures thereof. The amount of the pure ionones or the mixtures thereof in the composition is at least 80% by weight, in particular at least 90% by weight, for example at least 95% by weight.

Generally, the ionone used as starting material in the condensation reaction can be produced using well established processes or can be readily obtained from commercially sources.

Generally, the aldehyde $R^1$—(C═O)H used in step i) of the present process is selected from straight and branched $C_2$-$C_5$-alkanals. Preferably, the aldehyde $R^1$—(C═O)H used in step i) of the present process is selected from ethanal (acetaldehyde), propanal, n-butanal, 2-methylbutanal, n-pentanal and 3-methylbutanal. More preferably, the aldehyde $R^1$—(C═O)H is selected from ethanal, propanal, n-butanal and 2-methylbutanal. It is particularly preferred, that the aldehyde $R^1$—(C═O)H used in step i) of the present process is ethanal.

Generally, the alcohol $R^2$—OH used in step i) of the present process is selected from straight and branched $C_1$-$C_6$-alkanols. Preferably, the alcohol $R^2$—OH is selected from methanol, ethanol, n-propanol, isopropanol, n-butanol, isobutanol, sec-butanol, tert-butanol, n-pentanol, n-hexanol and mixtures thereof. More preferably, the alcohol $R^2$—OH is selected from methanol, ethanol, n-propanol, isopropanol, n-butanol, tert-butanol and mixtures thereof. It is particularly preferred, that the alcohol $R^2$—OH used in step i) of the present process is selected from methanol, ethanol or isopropanol.

The condensation reaction can be carried out in the absence of, or in the presence of, any added solvent different from $R^2$—OH.

If the dimerization reaction is carried out in the presence of a solvent different from $R^2$—OH, it is preferable that the organic solvent used is inert under the reaction conditions. Among these are by way of example aliphatic hydrocarbons, halogenated aliphatic hydrocarbons, and aromatic and substituted aromatic hydrocarbons and ethers. It is preferable that the solvent is one selected from pentane, hexane, heptane, ligroin, petrol ether, cyclohexane, dichloromethane, trichloromethane, tetrachloromethane, benzene, toluene, xylene, chlorobenzene, dichlorobenzenes, dibutyl ether, THF, 1,4-dioxane, 1,2-dimethoxyethane and mixtures thereof.

It is preferred that the condensation reaction is carried out in the absence of any added solvent different from $R^2$—OH.

The condensation reaction can generally take place at ambient pressure, reduced pressure, or elevated pressure. It is preferable that the condensation reaction is carried out at ambient pressure.

Generally, the condensation reaction is carried out in the temperature range from −10 to 50° C., preferably in the temperature range from −5 to 40° C. Particularly, the condensation reaction is carried out in the temperature range from 0 to 30° C.

The condensation reaction can take place in the absence of or in the presence of an inert gas. The expression inert gas generally means a gas which under the prevailing reaction conditions does not enter into any reactions with the starting materials, reagents, or solvents participating in the reaction, or with the resultant products. It is preferable that the condensation reaction takes place without addition of any inert gas.

In a preferred embodiment of the condensation reaction, the composition containing α-ionone, β-ionone or γ-ionone or a mixture thereof is placed together with the aldehyde R'—(C=O)H into a suitable reaction vessel. Then a mixture of the alcohol $R^2$—OH and the metal hydroxide is added. The resulting reaction mixture is stirred for one to several hours, e.g. from 1 to 10 hours, preferably from 1 to 7 hours.

It is preferable, that the reaction conditions, in particular the amount of base, the reaction temperature and the reaction time, are chosen such that the conversion rate of the ionone is in the range of 10 to 98%, preferably in the range of 30 to 90%, more preferably in the range of 50 to 85%, in particular in the range of 65 to 85%.

The condensation product obtained in step i) of the present process may be a single compound or a mixture of two or more compounds of the general formula (I.a). Frequently, the condensation product obtained in step i) is a mixture of two compounds of the general formula (I.a). Typically, the condensation product is obtained as a mixture of the beta-alkoxyalkenone and the corresponding beta-hydroxyalkenone, where the beta-alkoxyalkenone is present in excess. Specifically, the condensation product is obtained as a mixture of the beta-alkoxyalkenone and the corresponding beta-hydroxyalkenone, where the beta-alkoxyalkenone is present in an amount of at least 60% by weight, preferably in an amount of at least 80% by weight or more, e.g. 90% by weight, based on the total amount of the beta-alkoxyalkenone and the corresponding beta-hydroxyalkenone.

Preferably, the condensation product comprises the beta-alkoxyalkenone in an amount of from 80 to 99.9% by weight, more preferably in an amount of from 85 to 99.9% by weight, in particular of from 90 to 99% by weight.

Step i) of the present process may further involve the purification of the condensation products by distillation or by using other purification methods such as column chromatography.

Step ii)

In step ii) of the present process, the reaction product obtained in step i) is treated with an acid to yield a ketone of the general formula (I.b) upon elimination of water and/or the alcohol $R^2$—OH. The elimination reaction, corresponding to step ii) of the present process, can be carried out using processes that are well known to the person skilled in the art.

Generally, the elimination is performed in the presence of an acid. Suitable acids are by way of example mineral acids, such as sulfuric acid, hydrochloric acid or phosphoric acid, organic acids, such as acetic acid, formic acid, trifluoroacetic acid, or sulfonic acids, such as methanesulfonic acid or p-toluenesulfonic acid.

The elimination reaction can either be performed using the purified condensation products of the general formula (I.a) or by directly using the reaction mixture obtained in step i) of the present process.

In a preferred embodiment of the present invention, the reaction mixture of step i), which contains at least one compound of the general formula (I.a), is directly applied in step ii) of the present process. In this regard, the term "directly" means that the reaction mixture is applied into step ii) of the present process without extracting the reaction mixture and without purifying the reaction mixture in another way.

In this preferred embodiment, the elimination reaction may also be conducted in the form of an acidic workup of the reaction mixture of step i), where the acid, in particular the mineral acids, is applied as an aqueous solution.

The side products of the elimination (water and/or the alcohol $R^2$—OH) can easily be separated from the target reaction product, e.g. by distillation.

Step iii)

Step iii) of the process according to the present invention comprises the hydrogenation of the ketone I.b obtained in step ii) with hydrogen in the presence of a hydrogenation catalyst. The catalytic hydrogenation is carried out using processes and catalysts for the hydrogenation of double bonds that are well known to the person skilled in the art.

Suitable catalysts for the hydrogenation of double bonds are for example catalysts, which comprise at least one metal of transition group VIII of the Periodic Table of the Elements, for example platinum, rhodium, palladium, cobalt, nickel, or ruthenium, preferably ruthenium or palladium, either alone or together with at least one metal from transition group I or VII of the Periodic Table of the Elements, for example copper or rhenium. The transition metal is typically deposited on a support material. Generally, any support material that is described in the state of the art for such catalysts can be used. Suitable support materials are by way of example single or mixed metal oxides, such as zirconium dioxide ($ZrO_2$), zinc oxide (ZnO), magnesium oxide (MgO), titanium dioxide ($TiO_2$), aluminum oxide, $TiO_2$—$Al_2O_3$, $ZrO_2$—$Al_2O_3$ or aluminosilicates, silicium dioxide ($SiO_2$), phosphated aluminum oxide, sulfated zirconium dioxide, mixed metal oxides, hydrotalcite, silicium carbide (SiC), tungsten carbide (WC), charcoal, activated charcoal, carbon, sulfated carbon, diatomite, clay, aluminum phosphate, or barium sulfate, or else a combination thereof.

Other suitable catalysts are likewise nickel-based catalysts, such as Raney catalysts, preferably Raney nickel.

In a preferred embodiment of the present process, the hydrogenation catalyst comprises at least one metal selected from nickel, rhodium and palladium.

Typically, the metal contend of the supported hydrogenation catalyst is in the range of from 0.1 to 30% by weight, preferably in the range of from 0.5 to 20% by weight and in particular of from 1 to 15% by weight.

Typically, the hydrogenation catalyst is applied in an amount of from 0.1 to 20% by weight, preferably in an amount of from 0.5 to 15% by weight, based on the amount of compound 1.b in the reaction mixture.

The hydrogenation can take place by analogy with known hydrogenation processes for hydrogenating organic compounds which have similar functional groups, in particular in analogy to the hydrogenation processes described by Hibbert et al., J. Am. Chem. Soc., 1924, Vol. 46, pp. 119-130, and by Naves et al., Helv, Chim. Acta, 1943, Vol. 26, pp. 2151-2165. To this end, the organic compound in the form of liquid phase or gas phase, preferably in the form of liquid phase, is brought into contact with the catalyst in the presence of hydrogen. The liquid phase can by way of example be passed over a fluidized bed of catalyst (fluidized bed method) or can be passed over a fixed bed of catalyst (fixed bed method).

In the process of the invention, it is preferable that the hydrogenation takes place in a fixed-bed reactor.

The hydrogenation can be performed in the presence or in the absence of an organic solvent. If the hydrogenation is performed in the presence of an organic solvent, preference is given to organic solvents that are inert under the hydrogenation conditions. Suitable solvents that can be used in the hydrogenation reaction are for example aliphatic hydrocarbons, such as pentane, hexane, heptane, ligroin, petrol ether or cyclohexane, aromatic hydrocarbons, such as benzene, toluene or xylenes, esters, such as ethyl acetate, ethers such as methyl-tert.-butylether, dibutyl ether, tetrahydrofuran, 1,4-dioxane or 1,2-dimethoxyethane, lower alkanols, such as methanol, ethanol, isopropanol or tert.-butanol, dialkylene glycol, or mono- or diethers thereof, for example, as well as mixtures of the aforementioned organic solvents.

The hydrogenation generally takes place under elevated hydrogen pressure. Typically, the hydrogenation is performed at a hydrogen pressure in the range from 1 to 300 bar, preferably in the range from 50 to 300 bar, particularly in the range from 100 to 300 bar.

The hydrogenation is typically carried out at a temperature in the range from 20 to 300° C., preferably at a temperature in the range from 50 to 300° C.

When the hydrogenation is carried out in the absence of any external inert organic solvent, preference is given to hydrogen pressure in the range from 1 to 300 bar, particularly from 100 to 300 bar and temperature in the range from 20 to 300° C., preferably in the range from 100 to 300° C.

If the hydrogenation is carried out in the presence of external inert organic solvent, e.g. MeOH, the hydrogenation is typically carried out at a hydrogen pressure in the range from 1 to 180 bar and at a temperature in the range from 20 to 140° C.

The amount of hydrogen used for the hydrogenation is generally from 1 to 100 times the stoichiometric amount of hydrogen theoretically needed for the complete hydrogenation of the double bonds of the compounds of the general formula (1.b).

In one preferred embodiment of step iii) of the present process, the hydrogenation is carried out in an inert solvent and in the presence of a hydrogenation catalyst, selected from Raney-nickel, palladium on charcoal or ruthenium on charcoal, under a hydrogen atmosphere at a pressure of from 1 to 300 bar and at a temperature of from 20 to 300° C., where the hydrogenation catalyst is used in an amount of from 0.1 to 15% by weight, based on the amount of the applied compounds 1.b.

The hydrogenation can be designed to take place either continuously or else batchwise, preference being given here to the continuous design of the process. The batchwise hydrogenation can use a reaction apparatus conventionally used for this purpose, e.g. a stirred reactor. It is preferable that the hydrogenation of the invention is carried out continuously in fixed-bed reactors in upflow mode or downflow mode. The hydrogen here can be passed over the catalyst cocurrently with the solution of the starting material to be hydrogenated, or else in countercurrent.

Suitable apparatuses for conducting fluidized-bed-catalyst hydrogenation and fixed-bed-catalyst hydrogenation are known in the prior art, e.g. from Ullmanns Enzyklopädie der Technischen Chemie [Ullmann's Encyclopedia of Industrial Chemistry], 4$^{th}$ edition, volume 13, pp. 135 ff., and also from P. N. Rylander, "Hydrogenation and Dehydrogenation" in Ullmann's Encyclopedia of Industrial Chemistry, 5th edn. on CD-ROM.

In a preferred embodiment of the present process the steps i) and ii) or the step iii) or all steps i) to iii) are performed in a continuous manner.

The process of the present invention may further comprise the purification of the compounds of the general formula (I) obtained in step iii), e.g. by distillation.

Preferred distillation devices for the purification of the compounds of the general formula (I) are for example distillation columns, such as tray columns optionally equipped with bubble cap trays, sieve plates, sieve trays, packages or filler materials, or spinning band columns, such as thin film evaporators, falling film evaporators, forced circulation evaporators, Sambay evaporators, etc. and combinations thereof. Especially preferred distillation devices for the purification of the compounds of the general formula (I) are distillation columns, in particular spinning band columns.

After distillative purification the compounds of the general formula (I) can typically be obtained in high purity, e.g. in a purity of at least 80%. Generally, the compounds of the general formula (I) obtained as a mixture of eight stereoisomers, as defined above.

Novel Compounds 1.a

The present invention further relates to compounds of the general formula (I.a), where $R^1$ is $C_1$-$C_4$-alkyl and $R^2$ is $C_1$-$C_6$-alkyl.

It is apparent from formula (I.a) that the carbon atom of the 5-position of the alkyl chain, which carries the alkoxyl group, may have (R)- or (S)-configuration. Furthermore, the double bond between the carbon atoms at position 1 and 2 of the alkyl chain may have E- or Z-configuration. Hence the compounds (I.a), as defined above, can be present in the form of the (1E,5R)-, (1E,5S)-, (1Z,5R)- or the (1Z,5S)-isomer or in the form of mixtures of these stereoisomers, hereinafter termed (1E/Z,5R/S)-isomer mixtures.

Thus, the present invention relates to both, the (1E,5R)-, (1E,5S)-, (1Z,5R)- or the (1Z,5S)-stereoisomers of the compounds (I.a), where $R^1$ is $C_1$-$C_4$-alkyl and $R^2$ is $C_1$-$C_6$-alkyl, as well as to mixtures of these stereoisomers.

Typically, the compounds (I.a), as defined above, are present as (1E/Z,5R/S)-stereoisomer mixtures. Frequently, the compounds (1.a), where $R^1$ is $C_1$-$C_4$-alkyl and $R^2$ is $C_1$-$C_6$-alkyl, are present in the form of (1E/Z,5R/S)-stereoisomer mixtures, which predominantly contains the (1E,5R)- and (1E,5S)-isomers, or in the form of a mixture of their (1E,5R)- and (1E,5S)-stereoisomers, which does not contain the corresponding Z-isomers, hereinafter termed (1E,5R/S)-stereoisomer mixtures.

Preferably, the present invention relates to compounds (I.a), where $R^1$ is $C_1$-$C_3$-alkyl and $R^2$ is $C_1$-$C_4$-alkyl.

More preferred are compounds of the general formula (I.a), where $R^1$ is methyl or ethyl and $R^2$ is methyl, ethyl, propyl, isopropyl, n-butyl or tert-butyl.

A particularly preferred embodiment of the present invention relates to compounds of the general formula (I.a), where $R^1$ is methyl and $R^2$ is $C_1$-$C_3$-alkyl.

An especially preferred compound of the general formula (I.a) is 5-methoxy-1-(2,6,6-trimethylhexen-1-yl)hex-1-en-3-one. This includes the pure (1E,5R)-, (1E,5S)-, (1Z,5R)- or (1Z,5S)-stereoisomers of 5-methoxy-1-(2,6,6-trimethylhexen-1-yl)hex-1-en-3-one as well as the (1E/Z,5R/S)- and (1E,5R/S)-stereoisomer mixtures thereof, as defined above.

As previously mentioned, it has surprisingly been found that the compounds of the general formula (I.a), where $R^1$ is $C_1$-$C_4$-alkyl and $R^2$ is $C_1$-$C_6$-alkyl, possesses advantageous sensory properties, in particular a pleasant odor.

Therefore, the present invention further relates to the use of a compound of the general formula (I.a), where $R^1$ is $C_1$-$C_4$-alkyl and $R^2$ is $C_1$-$C_6$-alkyl, as defined above, as a fragrance or as flavor.

Intensive odor impressions are to be understood as meaning those properties of aroma chemicals which permit a precise perception even in very low gas-space concentrations. The intensity can be ascertained via a threshold-value determination. A threshold value is the concentration of a substance in the relevant gas space at which an odor impression can just still be perceived by a representative test panel, although it no longer has to be defined. The substance class known as probably one of the most odor-intensive, i.e. those with very low threshold values, are thiols, whose threshold value is in the ppb/m$^3$ range. It is the aim of the search for new aroma chemicals to find substances with the lowest possible threshold value in order to permit the lowest possible use concentration. The closer one comes to this target, the more one talks of "intensive" odor substances or aroma chemicals.

"Pleasant odors" or "Advantageous sensory properties" are hedonic expressions which describe the niceness and preciseness of an odor impression conveyed by an aroma chemical.

"Niceness" and "preciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also describe the odor of musk or sandalwood. "Preciseness" generally refers to a spontaneously brought about sensory impression which—for the same test panel—brings about a reproducibly identical reminder of something specific.

For example, a substance can have an odor which is spontaneously reminiscent of that of an "apple": the odor would then be precisely of "apples". If this apple odor were very pleasant because the odor is reminiscent, for example, of a sweet, fully ripe apple, the odor would be termed "nice". However, the odor of a typically tart apple can also be precise. If both reactions arise upon smelling the substance, in the example thus a nice and precise apple odor, then this substance has particularly advantageous sensory properties.

The invention further relates to the use of a compound of the general formula (I.a), where $R^1$ is $C_1$-$C_4$-alkyl and $R^2$ is $C_1$-$C_6$-alkyl, as defined above, in products and/or compositions, which typically comprise at least one aroma compound, i.e. at least one fragrance and/or flavoring. Such compositions include, for example, laundry detergents, fabric detergents, cosmetic preparations, other fragranced hygiene articles, such as diapers, sanitary towels, armpit pads, paper towels, wet wipes, toilet paper, pocket tissues, and the like, foods, food supplements, examples being chewing gums or vitamin products, fragrance dispensers, examples being room air fresheners, perfumes, pharmaceutical preparations, and also crop protection products.

Typically, these compositions are formulated by incorporating a compound of the general formula (I.a), where $R^1$ is $C_1$-$C_4$-alkyl and $R^2$ is $C_1$-$C_6$-alkyl, as defined above, optionally together with one or more other aroma compounds, into an existing preparation, which before comprises no aroma compound or which before comprises one or more other aroma compound different from the compounds of the general formula (I.a), where $R^1$ is $C_1$-$C_4$-alkyl and $R^2$ is $C_1$-$C_6$-alkyl. Such compositions generally further comprise a carrier, which may be a compound, a compound mixture or other additives, which have no or no noticeable sensory properties. The carrier may as well be a compound or an additive having noticeable sensory properties, or a compound mixture comprising one or more other aroma compounds different from compounds of the general formula (I.a), where $R^1$ is $C_1$-$C_4$-alkyl and $R^2$ is $C_1$-$C_6$-alkyl, and optionally one or more compounds having no or no noticeable sensory properties.

In the compositions according to the present invention the compounds I.a, as defined above, are usually applied in amounts customary for formulation auxiliaries. More specifically the amount of the compound I.a is in the range of 0.001 to 50% by weight, in particular in the range of 0.01 to 20% by weight, especially in the range of 0.1 to 10% by weight, based on the total amount of the composition.

The compounds I.a, as defined above, preferably find use in laundry detergents and fabric detergents, in cosmetic preparations and in other fragranced hygiene articles. Particular preference is given to the use of the compounds I.a, as defined above, in cosmetic preparations such as perfumes and fragrances hygiene articles.

The invention further relates to a method of imparting or modifying a scent or a flavor to a composition, which method comprises including or incorporating at least one compound of the general formula (I.a), where $R^1$ is $C_1$-$C_4$-alkyl and $R^2$ is $C_1$-$C_6$-alkyl, into a composition in such an amount that imparts or modifies the scent or flavor of the composition. The total amount of the compound of the general formula (I.a), where $R^1$ is $C_1$-$C_4$-alkyl and $R^2$ is $C_1$-$C_6$-alkyl, required for modification depends on the nature and on the application purpose of the composition and can, therefore, vary in a wide range. Typically, the total amount of the compound 1.a included/incorporated into the composition is in the range from 0.001 to 50% by weight, in particular in the range from 0.01 to 20%.

The intensively and precisely smelling compounds of the general formula (I.a), where $R^1$ is $C_1$-$C_4$-alkyl and $R^2$ is $C_1$-$C_6$-alkyl, are preferably used as fragrance. Suitable fields of application are all applications in which a certain odor is desired, whether it is to mask more unpleasant odors or to generate a certain odor or certain odor notes in a targeted manner.

Therefore, the invention further relates to a fragrance containing composition and/or a fragranced product, which contains at least one compound of the general formula (I.a), where $R^1$ is $C_1$-$C_4$-alkyl and $R^2$ is $C_1$-$C_6$-alkyl, and a carrier material.

The total concentration of the compounds I.a, as defined above, in the fragrance containing composition and/or the fragranced product, according to the present invention, is not particularly limited. It can be changed in a wide range, depending on the purpose of their use. Generally, amounts that are customary for fragrances are used. The total amount of the compounds 1.a in the fragrance containing composition and/or the fragrance material is typically in the range from 0.001 to 20% by weight, in particular in the range from 0.01 to 10% by weight.

The carrier material may be a compound, a compound mixture or other additives having the properties as defined above. Suitable carrier materials may comprise liquid or oil-based carrier materials as well as wax-like or solid carrier materials.

Suitable liquid or oil-based carrier materials are for example selected from water, alcohols, such as ethanol, aliphatic diols and polyols having melting temperatures below 20° C., such as ethylene glycol, glycerol, diglycerol, propylene glycol, dipropylene glycol, cyclic siloxanes (silicon fluids), such as hexamethylcyclotrisiloxane or decamethylcyclopentasiloxane, plant-oils, such as fractionated coconut-oil, or esters of fatty alcohols having melting temperatures below 20° C., such as myristyl acetate or myristyl lactate, and alkyl esters of fatty acids having melting temperatures below 20° C., such as isopropyl-myristate.

Suitable wax-like or solid carrier materials are for example selected from fatty alcohols having melting temperatures above 20° C., such as myristyl alcohol, stearyl alcohol or cetyl alcohol, polyols and esters of fatty alcohol having melting temperatures above 20° C., synthetic petroleum derived waxes, such as paraffin waxes, water insoluble porous minerals, such as silica, silicates, for example talc, microporous aluminasilicate minerals (zeolites), clay minerals, for example bentonite, or phosphates for example sodium tripolyphosphate, paper, cardboard, wood, nonwoven of rayon staple fibers or fiber-fleeces.

Suitable carrier materials are for example also selected from water-soluble polymers, such as polyacrylic acid esters or quaternized polyvinyl pyrrolidone or water-alcohol-soluble polymers, such as specific thermoplastic polyesters and polyamides. The polymeric carrier material can be present in different forms, for example in form of a gel, a paste, or water insoluble solid particles, such as microcapsules or friable coatings.

Depending on the purpose of use, the carrier materials may further comprise other additives or auxiliaries, for example surfactants or mixtures of surfactants, viscosifiers, such as polyethylene glycols with a molecular weight of 400 to 20000 Da, lubricates, binding or agglomerating agents, such as sodium silicate, dispersing agents, detergent builder salts, filler salts, pigments, dyes, optical brighteners, anti-redeposition agents and the like.

Typical applications of the composition and/or the fragranced products according to the present invention are in the field of laundry and cleaning detergents, preparations of fragrances for the human or animal body, for rooms such as kitchens, wet rooms, automobiles or heavy goods vehicles, for real or artificial plants, for clothing, for shoes and shoe insoles, for items of furniture, for carpets, for air humidifiers and air fresheners, for cosmetics such as perfumes.

The invention also includes odorant combinations which comprise one or more compounds of the general formula (I.a), where $R^1$ is $C_1$-$C_4$-alkyl and $R^2$ is $C_1$-$C_6$-alkyl, as component A and at least one further compound known as an odorant or aroma substance, as component B, such as, for example, one or more of the following compounds B1 to B11:

B1: methyl dihydrojasmonate (e.g. hedione),
B2: 4,6,6,7,8,8-hexamethyl-1,3,4,6,7,8-hexahydrocyclopenta[g]benzopyran (e.g. Galaxolide™),
B3: 2-methyl-3-(4-tert-butylphenyl)propanal (Lysmeral™),
B4: 2-methyl-3-(4-isopropylphenyl)propanal (cyclamenaldehyde),
B5: 2,6-dimethyl-7-octen-2-ol (dihydromyrcenol),
B6: 3,7-dimethyl-1,6-octadien-3-ol (linalool),
B7: 3,7-dimethyl-trans-2,6-octadien-1-ol (geraniol),
B8: 2,3,8,8-tetramethyl-1,2,3,4,5,6,7,8-octahydro-2-naphthalenyl methyl ketone (Iso E Super™),
B9: alpha-hexylcinnamaldehyde,
B10: 3,7-dimethyl-6-octen-1-ol (citronellol),
B11: alpha- or beta- or delta-damascone.

Suitable formulations of odor substances are, for example, the formulations disclosed in JP 11-071312 A, paragraphs [0090] to [0092]. The formulations from JP 11-035969 A, paragraphs [0039] to [0043] are also likewise suitable.

EXAMPLES

I) Gas Chromatographic Analysis

GC-System and Separation Method:
GC-system: Agilent 6890N
GC-Column: HP-5 (30 m (Length), 0.32 mm (ID), 0.20 μm (FD))
Temperature program: 60° C. to 250° C. in 6° C./min, 20 minutes at 250° C., injector temperature 250° C., detector temperature 280° C.

II) Production Examples

Example II.1

Reaction of Beta-Ionone With Acetaldehyde

To a mixture of 30.0 g beta-ionone (0.26 mol) and 17.4 g (22 mL) acetaldehyde (0.39 mol) a solution of 15 g KOH (0.26 mol) in 100 mL methanol was added, while keeping the temperature between 5 to 10° C. The reaction mixture was then stirred for 4 hours at 15° C. until 65% conversion of beta-ionone was achieved. The reaction solution was analyzed by GC showing the presence of 40% methoxy compound and 20% aldol product along with 35% unreacted beta-ionone. The reaction mixture was neutralized with diluted acid and extracted with ethyl acetate. The organic layer was dried and the solvent was distilled off to obtain 58 g of a crude reaction mixture. The crude reaction product was purified by column chromatography, whereupon 17 g unreacted beta-ionone was recovered and 14 g 5-hydroxy-1-(2,6,6-trimethylcyclohexen-1-yl)hex-1-en-3-one (aldol product) and 16 g 5-methoxy-1-(2,6,6-trimethylcyclohexen-1-yl)hex-1-en-3-one (methoxy compound) was obtained. Both products were obtained in >95% purity (GC, area-% of the FID detector signal).

Example II.2

Elimination of Water in 5-hydroxyl-(2,6,6-trimethylaclohexen-1-yl)hex-1-en-3-one To the solution of 1 g of the hydroxy compound (aldol product) in TBME 0.3 mL of sulfuric acid were added and stirred for 4 hours. TLC showed complete conversion of starting material. The reaction mixture was washed with bicarbonate solution, crude yield=1 g. The crude was purified by flash chromatography to obtain 0.4 g desired product.

Elimination of Methanol in 5-methoxy-1-(2,6,6-trimethylcyclohexen-1-yl)hex-1-en-3-one A Mixture of 0.5 g of the methoxy compound in toluene and a catalytic quantity of para-toluenesulphonic acid (pTSA) (12 mg) were refluxed for 20 min. TLC showed the disappearance of the starting material. The reaction mixture was cooled to RT and washed with a saturated bicarbonate solution. On evaporation of solvent got 1 g crude product. Column chromatography gave 0.15 pure product.

III) Analytical Characterization

III.1) Analytical Characterization of 5-hydroxy-1-(2,6,6-trimethylcyclohexen-1-yl)hex-1-en-3-one The identity of 5-hydroxy-1-(2,6,6-trimethylcyclohexen-1-yl)hex-1-en-3-one was determined using high resolution GC-MS and $^1$H-$^{13}$C-1D/2D-NMR.
$^1$H-NMR-Analysis (300 MHz, CDCl$_3$):
Delta=7.35 (d, 1H), 6,2 (d, 1H), 3.85 (m, 1H), 3.3 (s, 3H), 2.95 (dd, 1H), 2.7 (dd, 1H), 2.15 (m, 2H), 1.75 (s, 3H), 1.6 (m, 2H), 1.5 (m, 2H), 1.2 (d, 3H), 1.05 (s, 6H).
$^{13}$C-NMR-Analysis (300 MHz, CDCl$_3$):
Delt=198.89, 142.76, 136.32, 136.01, 130.92, 73.72, 56.31, 47.25, 39.72, 34.04, 33.57, 28.79, 28.74, 21.76, 19.55, 18.38.

III.2) Analytical Characterization of 5-methoxy-1-(2,6,6-trimethylcyclohexen-1-yl)hex-1-en-3-one The identity of 5-methoxy-1-(2,6,6-trimethylcyclohexen-1-yl)hex-1-en-3-one was determined using high resolution GC-MS and $^1$H-$^{13}$C-1D/2D-NMR.

$^1$H-NMR-Analysis (300 MHz, CDCl$_3$):
Delta=7.35 (d, 1H), 6.2 (d, 1H), 3.3 (m, 1H), 2.0-2.9 (m, 12H), 2.1 (dd, 1H), 1.8 (s, 3H), 1.66 (m, 2H), 1.5 (m, 21-1), 1.2 (d, 3H), 1.05 (s, 6H).

$^{13}$C-NMR-Analysis (300 MHz, CDCl$_3$):
Delta=201.08, 143.28, 137.26, 135.90, 130.1, 64.12, 47.91, 39.73, 34.04, 33.66, 28.79, 28.76, 22.40, 21.76, 18.76.

IV) Scent Strip Tests

To evaluate the quality and intensity of the odor of 5-methoxy-1-(2,6,6-trimethylcyclohexen-1-yl)hex-1-en-3-one, scent strip tests were performed.

For this purpose strips of absorbent paper were dipped into solution containing 1 to 10 wt.-% 5-methoxy-1-(2,6,6-trimethylcyclohexen-1-yl)hex-1-en-3-one in ethanol. After evaporation of the solvent (about 30 sec.) the scent impression was olfactorically evaluated by a trained perfumer.

Scent Strip Test Results:
Odor Impression:
Intensity: 4, dry plum: 4, damascones: 3, sweet: 4, fruity: 3, tobacco: 2.
Volatility:
long lasting on blotter (>48 h)

As can be deduced from the scent strip test results, 5-methoxy-1-(2,6,6-trimethylcyclohexen-1-yl)hex-1-en-3-one is a olfactively valuable compound.

The invention claimed is:

1. A process for preparing a compound of formula (I),

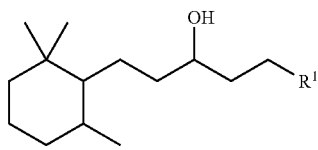

(I)

where R$^1$ is selected from C$_1$-C$_4$-alkyl, the process comprising:
i) reacting a composition containing α-ionone, β-ionone or γ-ionone or mixtures thereof with an aldehyde R$^1$—(C=O)H in the presence of a base and an alcohol R$^2$—OH to yield a reaction product mixture comprising at least one compound of formula (I.a),

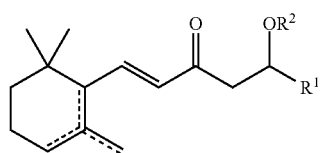

(I.a)

where
R$^2$ is C$_1$-C$_6$-alkyl, and
the broken lines represent a single double bond that can be arranged in one of the three positions drawn, ii) treating the reaction product obtained in step i) with an acid to yield a ketone of formula (I.b)

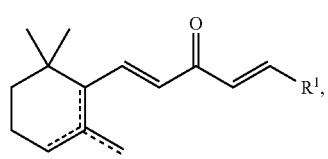

(I.b)

and
iii) hydrogenating the ketone I.b with hydrogen in the presence of a hydrogenation catalyst.

2. The process of claim 1, where the base used in step i) is selected from metal hydroxides.

3. The process of claim 1, where R$^1$ is methyl.

4. The process of claim 1, where the alcohol R$^2$—OH is selected from methanol, ethanol or isopropanol.

5. The process of claim 1, where the reacting step i) is performed at a temperature in a range of from −10 to 50° C.

6. The process of claim 1, where the reaction product mixture of the step i) is directly applied in step ii).

7. The process of claim 1, where the hydrogenation catalyst comprises at least one metal selected from the grout consisting of nickel, rhodium and palladium.

8. The process of claim 1, further comprising distilling a reaction mixture obtained in the step iii).

9. The process of claim 1, where the steps i) and ii) or the step iii), or all steps i) to iii), are performed in a continuous manner.

10. A compound of formula (I.a),

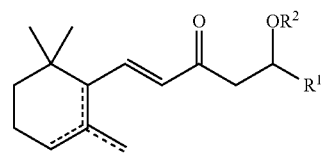

(I.a)

where
R$^1$ is C$_1$-C$_4$-alkyl,
R$^2$ is C$_1$-C$_6$-alkyl and
the broken lines represent a single double bond that can be arranged in one of the three positions drawn.

11. The compound according to claim 10, where R$^1$ is methyl and R$^2$ is C$_1$-C$_3$-alkyl.

12. The compound 5-methoxy-1-(2,6,6-trimethylhexen-1-yl)hex-1-en-3-one.

13. A fragrance or a flavor composition comprising
a) at least one compound (I.a), as defined in claim 10,
b) optionally at least one aroma chemical different from the compounds (I.a), and
c) optionally at least one carrier,
with the proviso that the composition comprises at least one of the components b) or c).

14. A product comprising at least one compound (I.a), as defined in in claim 10, the product selected from the group consisting of laundry detergents, fabric detergents, cosmetic preparations, fragranced hygiene articles, foods, food supplements, fragrance dispensers, perfumes, pharmaceutical preparations and crop protection compositions.

15. A method of imparting or modifying a scent or a flavor to a composition, which method comprises incorporating at least one compound of the formula (I.a), as defined in claim 10, into a composition in such an amount that imparts or modifies the scent or flavor of the composition.

* * * * *